United States Patent
Vogt et al.

(10) Patent No.: US 9,241,746 B2
(45) Date of Patent: Jan. 26, 2016

(54) ANTI-INFECTIVE SPACER FOR OSTEOSYNTHESIS PLATES

(71) Applicant: Heraeus Medical GmbH, Wehrheim (DE)

(72) Inventors: Sebastian Vogt, Erfurt (DE);
Klaus-Dieter Kühn, Marburg (DE)

(73) Assignee: Heraeus Medical GmbH, Wehrheim (DE)

( * ) Notice: Subject to any disclaimer, the term of this patent is extended or adjusted under 35 U.S.C. 154(b) by 295 days.

(21) Appl. No.: 13/799,870

(22) Filed: Mar. 13, 2013

(65) Prior Publication Data
US 2013/0267954 A1    Oct. 10, 2013

(30) Foreign Application Priority Data

Mar. 30, 2012    (DE) .......................... 10 2012 006 454

(51) Int. Cl.
*A61B 17/80* (2006.01)
*A61B 17/00* (2006.01)

(52) U.S. Cl.
CPC ... *A61B 17/8028* (2013.01); *A61B 2017/00889* (2013.01); *A61B 2017/00893* (2013.01); *A61F 2250/0067* (2013.01)

(58) Field of Classification Search
USPC ................................................. 606/280–299
See application file for complete search history.

(56) References Cited

U.S. PATENT DOCUMENTS

| 4,191,740 | A | | 3/1980 | Heusser et al. |
| 4,191,743 | A | | 3/1980 | Klemm et al. |
| 4,338,926 | A | * | 7/1982 | Kummer et al. ................. 606/70 |
| 5,084,051 | A | | 1/1992 | Törmälä et al. |
| 6,692,498 | B1 | * | 2/2004 | Niiranen et al. ................. 606/70 |
| 6,945,448 | B2 | * | 9/2005 | Medlin et al. ............. 228/248.1 |
| 7,842,037 | B2 | | 11/2010 | Schulze |
| 2003/0039676 | A1 | | 2/2003 | Boyce et al. |
| 2005/0169893 | A1 | * | 8/2005 | Koblish et al. ............... 424/93.7 |
| 2005/0246021 | A1 | | 11/2005 | Ringeisen et al. |
| 2006/0025848 | A1 | * | 2/2006 | Weber et al. ................. 623/1.15 |
| 2006/0085001 | A1 | | 4/2006 | Michelson |
| 2006/0224242 | A1 | * | 10/2006 | Swords et al. ............. 623/17.19 |

(Continued)

FOREIGN PATENT DOCUMENTS

| CN | 2303591 Y | 1/1999 |
| CN | 101152103 A | 4/2008 |

(Continued)

OTHER PUBLICATIONS

German Office Action for related German Appllication No. 10 2012 006 454.3 dated Dec. 7, 2012.

(Continued)

*Primary Examiner* — Matthew Lawson
(74) *Attorney, Agent, or Firm* — Norris McLaughlin & Marcus, P.A.

(57) ABSTRACT

The invention relates to an anti-infective spacer for osteosynthesis plates comprising a plate having at least one opening for accommodating a screw, whereby the plate is made up of at least one biocompatible material, in which at least one antimicrobial substance is distributed, dispersed or dissolved. The invention also relates to a set comprising at least one osteosynthesis plate and at least one said spacer, preferably comprising at least one screw for each recess of each spacer.

15 Claims, 2 Drawing Sheets

(56) References Cited

U.S. PATENT DOCUMENTS

Figure 1:
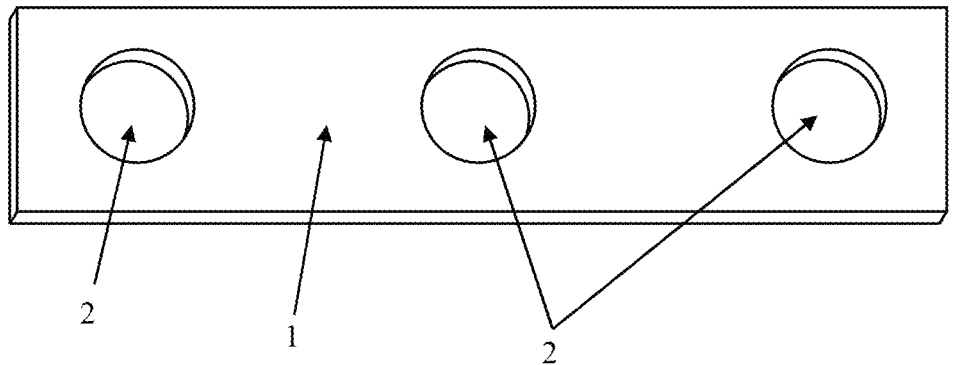

| | | |
|---|---|---|
| 2006/0293670 A1 | 12/2006 | Smisson, III et al. |
| 2007/0173840 A1 | 7/2007 | Huebner |
| 2007/0191848 A1* | 8/2007 | Wack et al. .................... 606/69 |
| 2008/0097432 A1 | 4/2008 | Schulze |
| 2008/0177330 A1* | 7/2008 | Ralph et al. .................. 606/290 |
| 2008/0262630 A1* | 10/2008 | Fulmer et al. ............... 623/23.52 |
| 2008/0317812 A1* | 12/2008 | Zhang et al. .................. 424/423 |
| 2009/0082816 A1 | 3/2009 | Graham et al. |
| 2009/0163958 A1* | 6/2009 | Tarcha et al. ................. 606/280 |
| 2010/0057128 A1* | 3/2010 | Bullard ......................... 606/246 |
| 2010/0268282 A1 | 10/2010 | Trieu |
| 2012/0053637 A1* | 3/2012 | Imwinkelried et al. ....... 606/281 |
| 2012/0215307 A1* | 8/2012 | Chen et al. ...................... 623/10 |

FOREIGN PATENT DOCUMENTS

| | | |
|---|---|---|
| DE | 2815934 A1 | 10/1979 |
| DE | 19511268 A1 | 10/1996 |
| DE | 202005020490 U1 | 3/2006 |
| EP | 0087662 A1 | 9/1983 |
| EP | 0170979 A2 | 2/1986 |
| EP | 0520177 A1 | 12/1992 |
| EP | 2005978 A1 | 12/2008 |
| JP | H01501289 A | 5/1989 |
| JP | 2009131611 A | 6/2009 |
| WO | 88 03417 A1 | 5/1988 |
| WO | 2007047420 A2 | 4/2007 |
| WO | 2011006228 A1 | 1/2011 |

OTHER PUBLICATIONS

Chinese Office Action for corresponding Chinese Application No. 201310106926.4 dated May 6, 2014.
European Search Report for corresponding European Application No. 13159841.9 dated Jul. 25, 2013.
English-language Translation of Japanese Office Action for corresponding Japanese Application No. 2013-059179 dated Feb. 4, 2014.
Canadian Office Action for corresponding Canadian Application No. 2,809,115 dated Apr. 24, 2014.
Australian Office Action for corresponding Australian Application No. 2013201995 dated Feb. 28, 2014.
Canadian Office Action for corresponding Canadian Application No. 2,809,115 dated Jan. 27, 2015.
EPO Search Report for corresponding EP Application No. 13159841.9 dated Dec. 17, 2014.

* cited by examiner

ANTI-INFECTIVE SPACER FOR OSTEOSYNTHESIS PLATES

BACKGROUND OF THE INVENTION (1) Field of the Invention

The invention relates to an anti-infective spacer for osteosynthesis plates comprising a plate having at least one recess for accommodating a screw, as well as a set comprising at least one osteosynthesis plate and at least one said spacer.

The term, osteosynthesis, is understood to refer to operative management of broken bones with implants, whereby implants made of biocompatible metal alloys are used most frequently. The aim of osteosynthesis is to mechanically fix reduced bone fragments during the healing phase. Said fixation enables the restoration of axis angles and articular positions of fractured bones.

Aside from nails, screws, Kirschner wires, osteosynthesis plates are used particularly frequently for osteosynthesis. Osteosynthesis plates are perforated plates made of biocompatible metal alloys. The openings in osteosynthesis plates are circular or oval in shape. Osteosynthesis plates are screwed to the ends of the fractured bones after these are reduced. The openings of the osteosynthesis plates are designed such that screw heads can be sunk, at least partially, into them. In this context, at least parts of the osteosynthesis plates contact the bone directly.

Osteosynthesis plates are usually screwed to both ends of the bone fragments using bicortical screws. However, the two-dimensional contact of osteosynthesis plates with the bone is a problem in that the contact pressure may cause necrosis of the periosteum (bone membrane) to become manifest. This was the rationale underlying the development of so-called "limited contact plates" (LCP). These osteosynthesis plates contact the periosteum only in spots or stripes. This means that the size of the contact surface of the osteosynthesis plates is reduced. Later on, so-called "dynamic compression plates" (DCP) and/or "limited contact dynamic compression plates" (LC-DCP) were developed. Said plates contain oval openings. Using screws with oval screw heads allows the screws to be tightened while concurrent compression of the bone fragments against each other is attained. Currently, so-called osteosynthesis plates with "angular stability" are available as well. Made of specialised metal alloys, these plates have a thread arranged right below the screw heads such that the screws are galled to the plate when the screws are tightened on the osteosynthesis plates. The osteosynthesis plate and the screws thus form a unit and a very stable mechanical connection is formed.

(2) Description of Related Art

Depots for local release of antimicrobial active substances have been known for decades. Accordingly, EP 0 170 979 A2 describes a depot based on gelatine. EP 0 087 662 A1 discloses an active substance depot that utilises tricalcium phosphate as carrier. Polymethylmethacrylate as carrier material for antimicrobial active substances is known from documents DE 28 15 934 A1, U.S. Pat. No. 4,191,743, and U.S. Pat. No. 4,191,740. Polymethylmethacrylate as a carrier of active substances has been introduced by Heraeus Medical and by Biomet as "Heraeus PMMA-Kette mit Gentamicin" (PMMA chain with gentamicin) and Septopal®, respectively.

A generic spacer for a bone plate is known from EP 2 005 978 B1 and comprises a coating containing a therapeutic agent, a polymer carrier, and a buffer medium. The coating is to induce bone healing and bone formation.

It is a disadvantage of known spacers that they do not have an antimicrobial effect. Moreover, the duration of the effect of the coating is limited and can be controlled only to a degree.

It would also be desirable to have a simple manufacturing process, in which no additional manufacturing steps are required in order to fabricate the spacer. There is always a need for inexpensive fabrication.

BRIEF SUMMARY OF THE INVENTION

It is the object of the present invention to overcome these and other disadvantages that have not been specified above. In particular, a reliable and long-lasting medical effect of the inserted spacers is to be attained. Moreover, the manufacturing of the spacers should be simple and inexpensive. It is also an object of the invention to develop an anti-infective spacer for osteosynthesis plates that ensures a safe distance between osteosynthesis plates and the bone in order to prevent pressure necrosis.

Said objects are met through an anti-infective spacer for osteosynthesis plates comprising a plate having at least one opening for accommodating a screw, in which the plate is made up of at least one biocompatible material, in which at least one antimicrobial substance is distributed, dispersed or dissolved.

In this context, the distribution or dispersion extends throughout the entire material, preferably extends homogeneously throughout the material. The distribution or dispersion can be contained in pores in the base material of the plate in this context. Preferably, the pores are essentially completely filled with a substance that contains the antimicrobial substances.

In this context, the invention can provide at least a sufficient amount and/or concentration of antimicrobial substance to be contained in the biocompatible material such that an antimicrobial effect can be attained at least at the surface of the plate, preferably an antimicrobial effect can be attained in a region extending beyond the surface of the plate.

This measure ensures that the anti-infective spacers have a positive bacteriostatic effect when they are inserted in a patient.

Moreover, the invention can provide the spacer to possess point-shaped or strip-shaped elevations on at least one side.

The elevations reduce the contact surface of the spacer and thus further reduce the danger of bone necrosis.

The invention can also provide the recesses to be circular and/or oval in shape.

These shapes provide for particularly simple handling even during the surgery. The oval shape affords a stronger connection of the spacer to a screw tightened inside it.

Particularly preferred embodiments of the invention can be characterised in that the spacer is made up of a plastic material or a porous metal or a porous ceramic material or a combination of said materials.

Moreover, the invention can provide the spacer to be made up of a plastic material from the group of polymethylmethacrylates, polymethylmethacrylate-co-methylacrylates or polymethylmethacrylate-co-styrenes and/or at least one radiopaquer to be contained, preferably be dispersed, in the plastic material, whereby the radiopaquer is particularly preferably selected from the group of barium sulfate, zirconium dioxide, and tantalum.

The polymers from the group of polymethylmethacrylates, polymethylmethacrylate-co-methylacrylates, and polymethylmethacrylate-co-styrenes are biocompatible, as has been demonstrated through their use in PMMA bone cements. Said plastic materials are easy to shape into plates through customary forming methods, such as injection moulding or pressing. Moreover, it is feasible just as well to use plate material of said plastic materials to produce spacers of different shapes through simple punching. It is particularly advantageous for the plastic material to have a radiopaque material admixed to it such that it is well visualised in a radiograph through its sufficient contrast. Barium sulfate, zirconium dioxide, and tantalum are particularly well-suited for this purpose. It is feasible just as well to admix organic iodine compounds as radiopaquer. Radiopaquer being incorporated allows the position of the spacers to be traced easily by radiological means.

According to another refinement, the invention can provide the spacer to be made up of a plastic material and the plastic material to contain an additive that enhances the release of the active substance, preferably calcium sulfate dihydrate, calcium sulfate, calcium carbonate, polyethylene glycol, mannitol, sorbitol, erythritol, dianhydroglucitol, anhydroglucitol, glycine and/or alanine.

Having the additive allows the amount of antimicrobial active substance that is dissolved or dispersed in the plastic material to be reduced or the release of the antimicrobial active substance to be enhanced.

According to another particularly preferred embodiment, the invention can provide the spacer to comprise a porous metal, preferably provides the spacer to be made up of a porous metal, whereby the pores in the metal are interconnecting and preferably have a pore diameter of 1-300 μm, particularly preferably have a pore diameter in the range of 1-100 μm.

This means that the hollow spaces of the pores can enclose antimicrobial substances which can be dissolved and/or are dissolvable upon contact with body fluids, such as wound exudations or blood. Spacers fabricated from porous metal are advantageous in that their compressive strength is very high.

The invention can provide the porous metal to be titanium, a titanium alloy, tantalum, a tantalum alloy or chromium-cobalt steel in this context.

Said metals are well-suited as material for spacers according to the invention due to their good biocompatibility and elasticity.

As an alternative to metallic spacers, the invention can provide the spacer to be made up of a porous ceramic material, whereby the pores are interconnecting and preferably have a pore diameter of 1-300 μm, particularly preferably have a pore diameter in the range of 1-100 μm.

In this context, the invention can provide the porous ceramic material to be aluminium oxide, zirconium dioxide, hydroxylapatite, wollastonite or tricalciumphosphate.

Ceramic materials are particularly hard and resistant to abrasion. The latter ceramic materials are resistant to pressure and biocompatible.

Particularly preferred and advantageous embodiments of the invention are characterised in that the antimicrobial substance is antibiotics, octenidine dihydrochloride, polyhexanide, chlorhexidine, trichlosan, quarternary ammonium salts, silver salts, silver oxide, copper salts or copper oxide or a mixture of said substances.

Referring to the antibiotics, in particular aminoglycoside antibiotics, such as gentamicin, tobramycin, and amikacin, are preferred.

Said antibiotics can be used both in the form of easily soluble salts, such as in the form of the sulfate, and in the form of poorly water-soluble forms, such as, for example, fatty acid salts, fatty alcohol sulfates or flavone phosphates. Using poorly soluble salts of antibiotics enables a delayed release of said antibiotics, which is particularly preferred. Moreover, said antibiotics salts also adhere well to metallic and ceramic surfaces.

Referring to the group of antiseptic active substances, octenidine dihydrochloride, polyhexanide, chlorhexidine, trichlosan, quarternary ammonium salts, silver salts, silver oxide, copper salts, and copper oxide are particularly well-suited.

According to another embodiment, the invention can provide the content of the antimicrobial substance in the spacer to be in the range of 0.1 to 80%, whereby the range from 0.1 to 40% is preferred and the range from 0.1 to 20% is particularly preferred.

One embodiment of a spacer according to the invention is a ring washer having one or more recess(es). Said ring washer can be circular or oval in shape or elongated in the form of a perforated plate having multiple recesses.

The objects of the invention are also met through a set comprising at least one osteosynthesis plate and at least one said spacer, preferably comprising at least one screw for each recess of each spacer.

One advantage of the set is that all components required for an operation for treatment of the bone fracture are provided together and match each other.

The invention is based on the surprising finding that the use of a material, as a spacer, that contains an antimicrobial substance that can be dissolved out of the material allows the spacer to be used not only for its other functions, but also for prevention of infections at the sites at which the spacers are placed, i.e. at the bone. Permanent release of antimicrobial agents also supports the prevention of pressure necrosis and/or mitigates the consequences of this complication upon the manifestation of pressure necrosis.

If designed appropriately, the spacer according to the invention can release at least one antimicrobially effective substance over a period of at least several days such that at least the surface of the spacer is protected from bacterial colonisation. The transition from the periosteum to the corticalis is particularly at risk of infection in plate osteosynthesis since microbial germs may migrate along the screws through the periosteum into the corticalis and then into the marrow. This can lead to the manifestation of osteitis/osteomyelitis and there is an attendant risk of chronification. The spacers according to the invention can be used to protect, by antimicrobial means, in particular the regions where the screws pass from the periosteum to the corticalis. Moreover, the spacer is biocompatible and inexpensive and simple to manufacture.

The spacer according to the invention can be used not only in osteosynthesis plates. It is also feasible to use said spacer in any other osteosynthesis material, in which screws are used, such as external fixators.

BRIEF DESCRIPTION OF THE SEVERAL VIEWS OF THE DRAWING(S)

Figure 2:
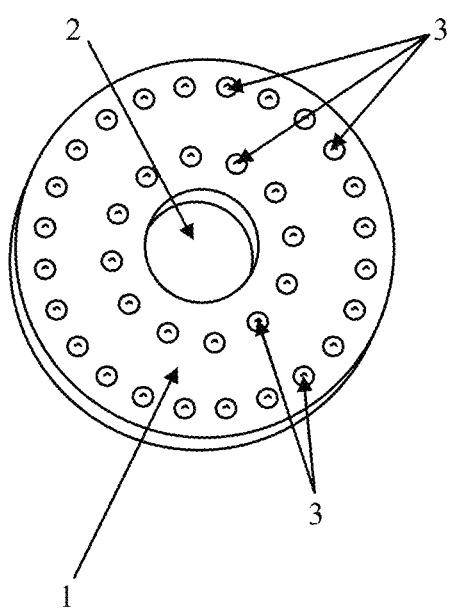
Figure 3:
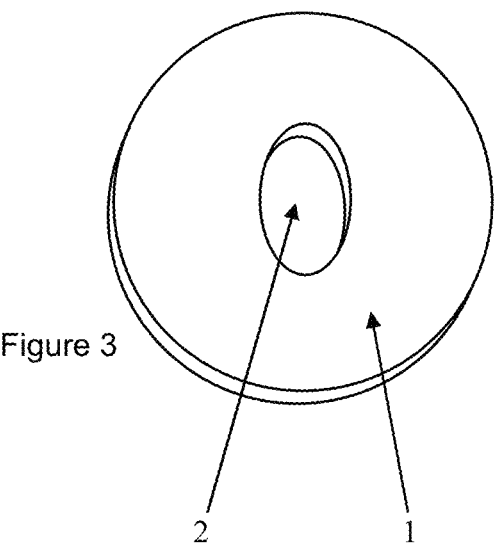
Figure 4:
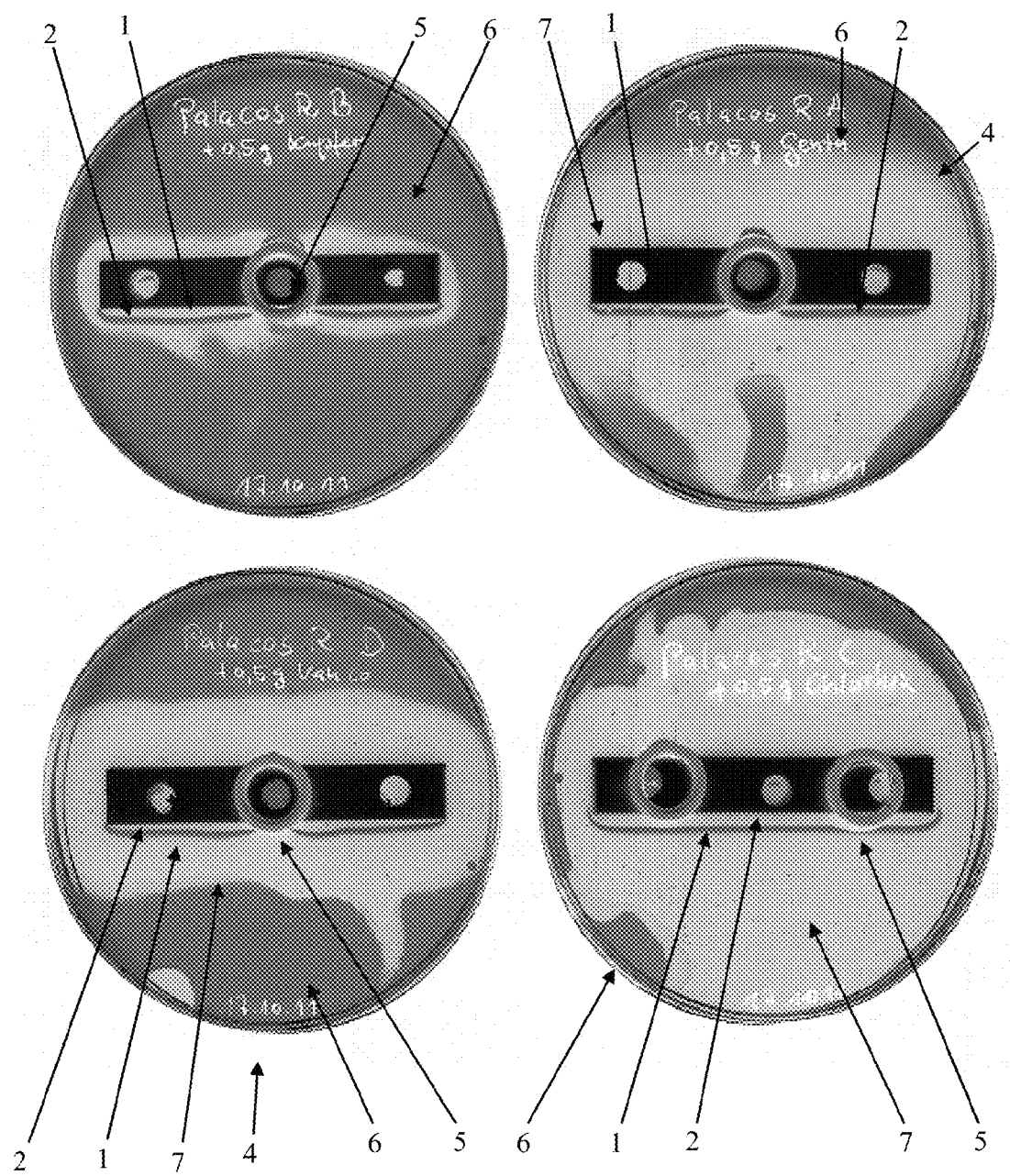

Exemplary embodiments of the invention shall be illustrated in the following on the basis of four schematic figures, though without limiting the scope of the invention. In the figures:

FIG. 1: shows a schematic perspective view of a spacer according to the invention having three recesses;

FIG. 2: shows a schematic perspective view of an alternative spacer according to the invention having one recess;

FIG. 3: shows a schematic perspective view of yet another spacer according to the invention having one recess; and FIG. 4: shows a view onto the medium in Petri dishes containing bacterial lawns and spacers according to the invention to illustrate the antimicrobial effect.

DETAILED DESCRIPTION OF THE INVENTION

FIG. 1 shows a schematic perspective view of a spacer 1 according to the invention having three recesses 2. The spacer 1 is 2.5 mm in thickness, 50 mm in width, and 10 mm in height. The recesses 2 are equidistant and circular. The diameter of the recesses 2 is 6 mm.

The spacer 1 is fabricated from a porous titanium alloy, whereby the interconnecting pores have an average cross-section of approximately 40 µm. The pores are essentially fully filled with a substance that comprises an antibiotic or a mixture of multiple antibiotics.

During a surgery, the spacer 1 is being arranged between an osteosynthesis plate and the bone, whereby the screws used to secure the osteosynthesis plate to the bone extend through the recesses 2 of the spacer 1. The spacer 1 keeps the osteosynthesis plate at a distance from the bone. A strip-shaped profile (not shown) is provided on the underside of the spacer 1 in the form of strip-shaped elevations by means of which the spacer 1 contacts the bone.

Due to the size of the pores and the composition of the substance itself, the antibiotic or antibiotics is/are released slowly but steadily from the inserted spacer 1. The antibiotic or antibiotics is/are dissolved out of the spacer by wound exudations and the blood of the patient.

FIGS. 2 and 3 show schematic perspective views of alternative spacers 1 according to the invention. The spacers 1 are shaped to be circular in the way of a ring washer. The spacer 1 according to FIG. 2 has a single central circular recess 2. A multitude of point-shaped elevations 3 by means of which the inserted spacer 1 contacts the bone are provided on the surface of the spacer 1. The aim of this measure is to minimise the contact surface in order to prevent bone necrosis. The spacer 1 according to FIG. 2 consists of a porous aluminium oxide ceramic material, whereby an antimicrobial substance comprising chlorhexidine is introduced into the pores which have an average diameter of 50 µm and are connected to each other (interconnecting pores).

The spacer 1 according to FIG. 3 has an oval recess 2. The purpose of recess 2 having an oval shape is to attain a stronger connection of the spacer 1 by means of one screw securing the spacer 1 and a corresponding osteosynthesis plate to the bone of a patient. The spacer 1 is made from a plastic material that contains an antimicrobial substance. In addition, the plastic material contains an additive comprising calcium sulfate dihydrate that enhances the release of the active substance.

FIG. 2 shows a top view onto the medium in four different Petri dishes 4, in which four different spacers 1, each having three recesses 2, are arranged on plastic rings 5. The plastic rings 5 keep the spacer 1 at a distance from the medium in the Petri dish 4. The media in the Petri dishes 4 are provided with a bacterial lawn 6 (dark peripheral region of the Petri dishes 4) that is suitable to support bacterial growth. Release of the antimicrobial substance from the spacers 1 according to the invention causes inhibitory zones 7 to arise in which the antimicrobial substance suppresses or prevents bacterial growth.

The four spacers according to the invention were produced as follows: In each case, 0.5 g of active substance were added to 20 g Palacos R (batch no. 7034) and the sample was then milled for 30 minutes in a plastic bottle in the presence of three porcelain milling beads using a Turbula mixer. Then, these mixtures were mixed with 10 ml Palacos monomer liquid each and strip-shaped spacers 1 having dimensions of 65 mm×10 mm×3.2 mm each containing three recesses 2 with a diameter of 5 mm were produced.

The following table shows the addition of active substance to the four different spacers 1.

| Example | Addition of active substance |
| --- | --- |
| 1 (top left) | 0.5 g Copper(II) sulfate (Sigma-Aldrich) |
| 2 (top right) | 0.5 g Gentamicin sulfate (Fujian Fukang) |
| 3 (bottom left) | 0.5 g Vancomycin hydrochloride (Abbott) |
| 4 (bottom right) | 0.5 g Chlorhexidine diacetate (Sigma-Aldrich) |

In order to determine the biological efficacy of the spacers 1, these were placed on sterile silicone rubber rings 5 in the Petri dishes 4 and CASO agar was poured around them such that the top side of the spacers 1 projected from the agar. The CASO agar contained 106 CFU/ml of a spore suspension of *Bacillus subtilis* ATCC 6633. The spacers 1 on the CASO agar were incubated for 20 hours at 35° C. For documentation purposes, the Petri dishes 4 were scanned and inverted (see FIG. 4) such that zones of inhibition 7 appear bright whereas the bacterial lawn 6 is dark.

The zones of inhibition 7 were then scanned and subsequently inverted. The zones of inhibition 7 are visible as bright areas.

In examples 1 to 4, a pronounced zone of inhibition 7 was detected around each spacer 1, whereby the size of the zones of inhibition 7 decreased in the order chlorhexidine diacetate, gentamicin, vancomycin, and copper(II) sulfate.

Accordingly, all four exemplary spacers 1 according to the invention can be used and can be used as spacers 1 for osteosynthesis plates on bones.

The features of the invention disclosed in the preceding description and in the claims, figures, and exemplary embodiments, can be essential for the implementation of the various embodiments of the invention both alone and in any combination.

LIST OF REFERENCE NUMBERS

1 Spacer
2 Recess
3 Elevation
4 Petri dish
5 Plastic ring
6 Bacterial lawn
7 Zone of inhibition

What is claimed is:

1. An anti-infective spacer (1) for osteosynthesis plates comprising:
   a plate having at least one recess (2) for accommodating a screw,
   the plate comprises at least one biocompatible material, in which at least one antimicrobial substance distributed, dispersed or dissolved extends throughout the entire material of the plate homogeneously, and
   the spacer (1) is made from one-of a plastic material, and the plastic material contains an additive that enhances the release of an active substance.

2. The anti-infective spacer (1) according to claim 1, wherein at least a sufficient amount and/or concentration of antimicrobial substance is contained in the bio compatible material such that an antimicrobial effect can be attained at the surface of the plate and extending beyond the surface of the plate.

3. The anti-infective spacer (1) according to claim 1, wherein the spacer (1) possesses point-shaped or strip-shaped elevations (3) on at least one side.

4. The anti-infective spacer (1) according to claim 1, wherein the spacer (1) is made from a plastic material from the group of polymethylmethacrylates, polymethylmethacrylate-co-methylacrylates or polymethylmethacrylate-co-styrenes and/or at least one radiopaquer is contained in the plastic material, whereby the radiopaquer is selected from the group of barium sulfate, zirconium dioxide, and tantalum.

5. The anti-infective spacer (1) according to claim 4, wherein the at least one radiopaquer is dispersed in the plastic material.

6. The anti-infective spacer (1) according to claim 4, wherein the plastic material of the spacer (1) contains at least one radiopaquer selected from the group of barium sulfate, zirconium dioxide, and tantalum.

7. The anti-infective spacer (1) according to claim 1, wherein the antimicrobial substance is antibiotics, octenidine dihydrochloride, polyhexanide, chlorhexidine, trichlosan, quarternary ammonium salts, silver salts, silver oxide, copper salts or copper oxide or a mixture of said substances.

8. A set comprising a plurality of osteosynthesis plates and a plurality of spacers (1) according to claim 1, comprising at least one screw for each recess (2) of each spacer (1).

9. The anti-infective spacer (1) according to claim 1, wherein the active substance is one of calcium sulfate dihydrate, calcium sulfate, calcium carbonate, polyethylene glycol, mannitol, sorbitol, erythritol, dianhydroglucitol, anhydroglucitol, glycine and/or alanine.

10. The anti-infective spacer (1) according to claim 1, wherein the spacer (1) has interconnected pores having a pore diameter of 1-300 μm.

11. The anti-infective spacer (1) according to claim 1, wherein the spacer (1) has interconnected pores, having a pore diameter of 1-100 μm.

12. The anti-infective spacer (1) according to claim 1, wherein the content of the antimicrobial substance in the spacer (1) is in the range of 0.1 to 40%.

13. The anti-infective spacer (1) according to claim 1, wherein the content of the antimicrobial substance in the spacer (1) is in the range of 0.1 to 20%.

14. An anti-infective spacer (1) for osteosynthesis plates comprising:
a plate having at least one recess (2) for accommodating a screw,
the plate comprises at least one biocompatible material, in which at least one antimicrobial substance is distributed, dispersed or dissolved extends throughout the entire material of the plate homogeneously, and
the spacer (1) is made from one of a plastic material, a porous metal, a porous ceramic material or a combination of said materials,
wherein the content of the antimicrobial substance in the spacer (1) is in the range of 0.1 to 80%.

15. A bone fixation system comprising:
an osteosynthesis plate securable to a bone via a screw;
an anti-infective spacer (1) configured to be disposed between the osteosynthesis plate and the bone to ensure a safe distance between the osteosynthesis plate and the bone to prevent pressure necrosis; the spacer (1) including a plate having at least one recess (2) for accommodating the screw; the plate comprises at least one biocompatible material, in which at least one antimicrobial substance distributed, dispersed or dissolved extends throughout the entire material of the plate homogeneously, and
the spacer (1) is made from one of a plastic material, a porous metal, a porous ceramic material or a combination of said materials.

* * * * *